US00PP32565P2

(12) United States Plant Patent
van Buren

(10) Patent No.: US PP32,565 P2
(45) Date of Patent: Dec. 1, 2020

(54) ***FESTUCA* PLANT NAMED 'FCB2017'**

(50) Latin Name: *Festuca glauca*
Varietal Denomination: FCB2017

(71) Applicant: Gerrit Johannes van Buren, Bonaire (NL)

(72) Inventor: Gerrit Johannes van Buren, Bonaire (NL)

( * ) Notice: Subject to any disclaimer, the term of this patent is extended or adjusted under 35 U.S.C. 154(b) by 0 days.

(21) Appl. No.: 16/602,520

(22) Filed: Oct. 22, 2019

(51) Int. Cl.
*A01H 5/12* (2018.01)

(52) U.S. Cl.
USPC ..... Plt./388

(58) Field of Classification Search
USPC ..... Plt./388
CPC ..... A01H 5/12
See application file for complete search history.

*Primary Examiner* — Annette H Para
(74) *Attorney, Agent, or Firm* — Penny J. Aguirre

(57) ABSTRACT

A new cultivar of *Festuca glauca* plant named 'FCB2017' that is characterized by its very compact plant habit, its blue-green foliage, and its stiff and non-cascading foliage.

2 Drawing Sheets

Botanical classification: *Festuca glauca.*
Varietal denomination: 'FCB2017'.

BACKGROUND OF THE INVENTION

The present invention relates to a new and distinct cultivar of *Festuca glauca* and will be referred to hereafter by its cultivar name, 'FCB2017'. 'FCB2017' is a new cultivar of perennial ornamental grass grown for container and landscape use.

The new cultivar, 'FCB2017' was discovered by the Inventor as chance seedling in October 2017 that was growing in a container in Loxley, Ala. The container had been planted from seed sown of *Festuca glauca* 'Beyond Blue' (not patented). The male parent is unknown.

Asexual propagation of the new cultivar was first accomplished by division under the direction of the Inventor in Loxely, Ala. in October 2017. Asexual propagation by division has shown that the characteristics of the new cultivar are stable and are reproduced true to type in successive generations.

SUMMARY OF THE INVENTION

The following traits have been repeatedly observed and are determined to be the characteristics of the new cultivar. These attributes in combination distinguish 'FCB2017' as a unique cultivar of *Festuca.*

1. 'FCB2017' exhibits a very compact plant habit.
2. 'FCB2017' exhibits blue-green foliage.
3. 'FCB2017' exhibits stiff and non-cascading foliage.

The parent of 'FCB2017', 'Beyond Blue', differs from 'FCB2017' in having a less compact plant habit. 'FCB2017' can also be compared to *Festuca glauca* cultivars 'Casca11' (U.S. Plant Pat. No. 23,307) and 'Bolder Blue' (not patented). 'Casca11' differs from 'FCB2017' in having a larger plant size, a cascading plant habit, and more silvery foliage. 'Bolder Blue' is similar in plant habit and in having non-cascading foliage, but differs from 'FCB2017' in having a larger plant size and foliage that is more blue in color.

BRIEF DESCRIPTION OF THE DRAWINGS

The accompanying colored photographs illustrate the overall appearance and distinct characteristics of the new

*Festuca*. The photographs were taken of a 24-month-old plants of 'FCB2017' as grown in a greenhouse in 10.5 cm containers in Loxley, Ala.

Figure 1:
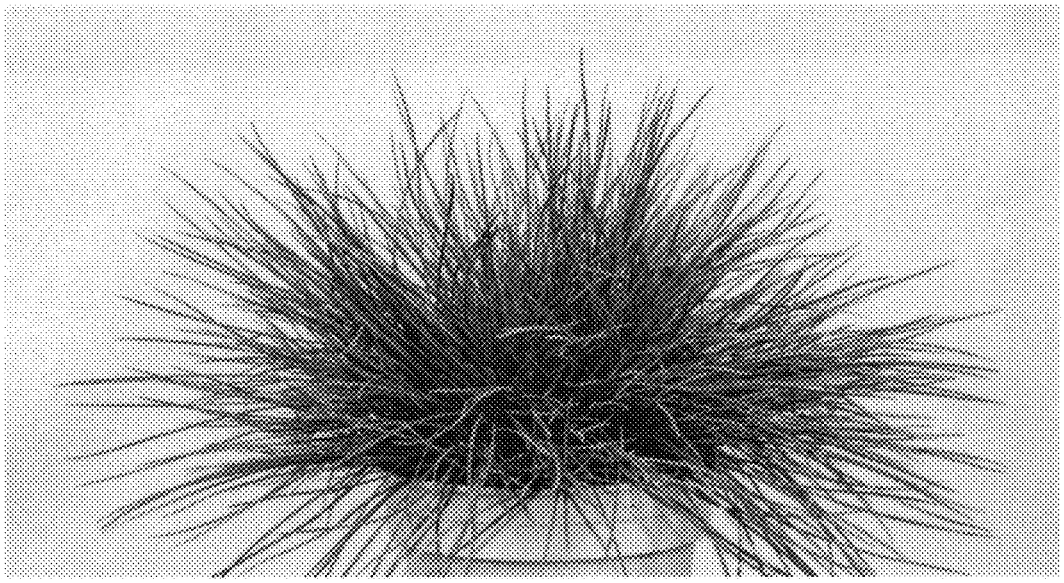

The photograph in FIG. 1 illustrates the overall plant habit and appearance of 'FCB2017'.

Figure 2:
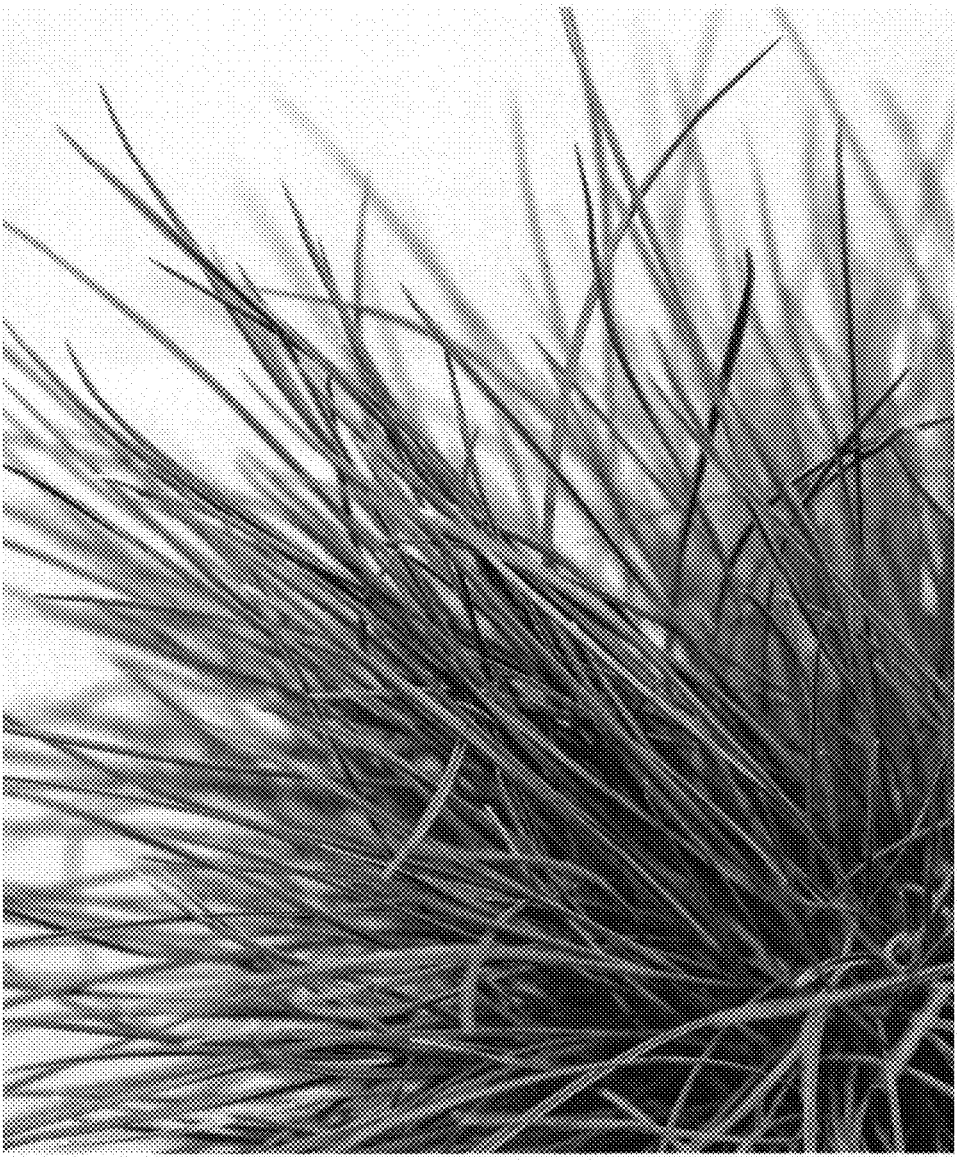

The photograph in FIG. 2 provides a detailed close-up view of the foliage of 'FCB2017'.

The colors in the photographs are as close as possible with the photographic and printing technology utilized and the color values cited in the detailed botanical description accurately describe the colors of the new *Festuca.*

DETAILED BOTANICAL DESCRIPTION

The following is a detailed description of 24-month-old plants of 'FCB2017' as grown in a greenhouse in a 10.5 cm container in Loxley, Ala. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Plant type.*—Evergreen to semi-evergreen perennial grass.

*Plant growth habit.*—Tight mound of stiff foliage, semi-erect with foliage upright to horizontal.

*Height and spread.*—Average of 13.5 cm in height and 28.7 cm in diameter.

*Hardiness.*—U.S.D.A. Zones 6 to 9.

*Diseases and pests.*—No susceptible or resistance to pests and diseases has been observed.

*Root description.*—Fibrous.

*Root development.*—Fully develops in 9-cm containers from a division in about 9 months.

*Plant ploidy.*—Diploid.

Growth and propagation:

*Propagation.*—Division.

*Time required for root initiation.*—Fully develop in 9-cm containers in about 9 months.

*Growth rate.*—Low to moderate.

*Branching.*—Main shoots grow from the base, no lateral branches.

Foliage description:

*Leaf shape.*—Linear.

*Leaf division.*—Simple.

*Leaf base.*—Sheathed.

*Leaf apex.*—Long and narrowly acuminate.

*Leaf aspect.*—Carinate, upright and outward.

*Leaf venation.*—Parallel, upper surface color; 136C, lower surface color; NN137B.

*Leaf margins.*—Entire.

*Leaf size.*—Average of 23 cm in length (up to 25 cm when fully expanded) and 1 mm in width.

*Leaf number.*—Average of 4 leaves per shoot.

*Leaf arrangement.*—Tufted, alternate growing in basal leafy shoots.

*Leaf surface.*—Both surfaces glabrous, matte and smooth, upper surface covered with a thin waxy layer; 122C and 122D in color.

*Sheath.*—Long and narrowly acuminate in aspect, average of 2.2 cm in length, 1.5 mm in width, color N144D and changing to 186D at the base.

*Leaf color.*—Young leaves upper and lower surface; 143C, changing to 144B at the base, mature leaves upper surface; 136C, mature leaves lower surface NN137B.

Flower description: No flowers have been observed to date.

Fruits and seeds: Seed production has not been observed to date.

It is claimed:

1. A new and distinct cultivar of *Festuca* plant named 'FCB2017' as herein illustrated and described.

* * * * *